US008927594B2

(12) United States Patent
Sheu et al.

(10) Patent No.: US 8,927,594 B2
(45) Date of Patent: Jan. 6, 2015

(54) COMPOUNDS FROM SOFT CORAL, METHOD OF PREPARATION AND PHARMACEUTICAL USES THEREOF

(75) Inventors: Jyh-Horng Sheu, Kaohsiung (TW); Wei-Hsien Wang, Kaohsiung (TW); Zhi-Hong Wen, Kaohsiung (TW); Bo-Wei Chen, Kaohsiung (TW); Ping-Jyun Sung, Pingtung (TW)

(73) Assignees: National Sun Yat-Sen University, Kaohsiung (TW); National Museum of Marine Biology & Aquarium, Pingtung (TW)

( * ) Notice: Subject to any disclaimer, the term of this patent is extended or adjusted under 35 U.S.C. 154(b) by 642 days.

(21) Appl. No.: 13/048,195

(22) Filed: Mar. 15, 2011

(65) Prior Publication Data

US 2012/0071547 A1 Mar. 22, 2012

(30) Foreign Application Priority Data

Sep. 16, 2010 (TW) .............................. 99131371 A

(51) Int. Cl.

| | |
|---|---|
| ***A61K 31/045*** | (2006.01) |
| ***A61K 31/35*** | (2006.01) |
| ***A61K 31/335*** | (2006.01) |
| ***C07D 313/00*** | (2006.01) |
| ***C07D 311/78*** | (2006.01) |
| ***C07D 307/00*** | (2006.01) |
| ***C07D 303/00*** | (2006.01) |
| ***C07C 35/00*** | (2006.01) |
| ***C07C 35/20*** | (2006.01) |
| ***C07C 35/22*** | (2006.01) |
| ***C07C 35/23*** | (2006.01) |
| ***C07C 69/18*** | (2006.01) |
| ***C07D 493/08*** | (2006.01) |
| ***A61K 35/56*** | (2006.01) |
| ***C07D 303/16*** | (2006.01) |
| ***C07D 307/87*** | (2006.01) |

(52) U.S. Cl.

CPC ................ *C07C 35/23* (2013.01); *C07C 69/18* (2013.01); *C07D 493/08* (2013.01); *A61K 35/614* (2013.01); *C07D 303/16* (2013.01); *C07D 307/87* (2013.01); *C07C 2102/32* (2013.01); *C07C 2103/26* (2013.01)

USPC ........... 514/450; 514/454; 514/469; 514/475; 514/729; 549/354; 549/386; 549/459; 549/462; 549/545; 568/700; 568/817; 568/819; 568/821

(58) Field of Classification Search

CPC .. C07D 313/00; C07D 311/78; C07D 307/93; C07D 307/79; C07D 303/14; C07D 303/16; C07C 35/23; C07C 35/205; A61K 31/047; A61K 31/35; A61K 31/336; A61K 31/343; A61K 31/352

USPC ......... 549/349, 459, 386, 512, 545, 354, 462; 568/700, 817, 819, 821; 514/450, 454, 514/469, 475, 729

See application file for complete search history.

(56) References Cited

PUBLICATIONS

Ahmed et al, Jol. Nat. Prod. (2005) vol. 68 No. 7 pp. 1051-1055.*
Office Action and Search Report issued Sep. 18, 2012 of the corresponding TW patent application No. 099131371 cites Journal of Natural Products, 2009.
English Abstract of Office Action and Search Report issued Sep. 18, 2012 of the corresponding TW patent application No. 099131371.
Shwu-Li Wu et al., "Simplexins A-I, Eunicellin-Based Diterpenoids from the Soft Coral Klyxum simplex", 2009, J. Nat. Prod., vol. 72, pp. 994-1000.
Bo-Wei Chen et al., Anti-inflammatory eunicellin-based diterpenoids from the cultured soft coral Klyxum simplex, Organic & Biomolecular Chemistry, 2010, pp. 2363-2366, vol. 8.
Bo-Wei Chen et al., Klysimplexins I-T, eunicellin-based diterpenoids from the cultured soft coral Klyxum simplex, Organic & Biomolecular Chemistry, 2011, pp. 834-844, vol. 9.
Bo-Wei Chen et al., Diterpenoids from the cultured soft coral Klyxum simplex, 240th American Chemical Society National Meeting, Boston, USA, Aug. 22-26, 2010, and 25th Symposium on Natural Products, Pingtung, Taiwan, Nov. 6-7, 2010.
Peter Libby, Inflammation and cardiovascular disease mechanisms, Am J Clin Nutr, 2006, pp. 456S-460S, vol. 83, USA.
Russell Ross, Atherosclerosis—Inflammatory Disease, The New England Journal of Medicine, Jan. 14, 1999, pp. 115-126, vol. 340, No. 2.
Andrew D. Lucas et al., Atherosclerosis: role of chemokines and macrophages, Expert Reviews in Molecular Medicine, Nov. 5, 2001, pp. 1-18, vol. 5.
Siamon Gordon, The macrophage, BioEssays, 1995, pp. 977-986, vol. 17, No. 11.
F. Cipollone, COX-2 and prostaglandins in atherosclerosis, LUPUS, 2005, pp. 756-759, vol. 14.
J.J. Boyle, Macrophage Activation in Atherosclerosis: pathogenesis and Pharmacology of Plaque Rupture, Current Vascular Pharmacology, 2005, pp. 63-68, vol. 3, No. 1.
Christopher S.R. Baker et al., Cyclooxygenase-2 Is Widely Expressed in Atherosclerotic Lesions Affecting Native and Transplanted Human Coronary Arteries and Colocalizes With Inducible Nitric Oxide Synthase and Nitrotyrosine Particularly in Macrophages, Arteriosclerosis, Thrombosis, and Vascular Biology, 1999, pp. 646-655, vol. 19.

(Continued)

*Primary Examiner* — Andrew D Kosar
*Assistant Examiner* — Raymond Covington
(74) *Attorney, Agent, or Firm* — WPAT, P.C.; Anthony King; Kay Yang

(57) ABSTRACT

The invention relates to compounds from the soft coral and the generation thereof. The invention also relates to the uses of the compounds from the soft coral in inhibiting inducible nitric oxide synthase and/or cyclooxygenase-2 and in treating the diseases associated with inducible nitric oxide synthase and/or cyclooxygenase-2.

7 Claims, 2 Drawing Sheets

(56) References Cited

PUBLICATIONS

L. D. K. Buttery et al., Inducible Nitric Oxide Synthase is Present within Human Atherosclerotic Lesions and Promotes the Formation and Activity of Peroxynitrite, Laboratory Investigation, Jul. 1996, pp. 77-85, vol. 75, No. 1.

Michael E. Burleigh et al., Cyclooxygenase-2 Promotes Early Atherosclerotic Lesion Formation i LDL Receptor-Deficient Mice, Circulation, 2002, pp. 1816-1823, vol. 105.

Toshio Hayashi et al., Selective iNOS inhibitor, ONO1714 successfully retards the development of high-cholesterol diet induced atherosclerosis by novel mechanism, Atherosclerosis, 2006, pp. 316-324, vol. 187.

Marco E. Turini et al., Cyclooxygenase-2: A Therapeutic Target, Annu. Rev. Med., pp. 35-57, vol. 53, (2002).

Rachel L.C. Handy et al., A comparison of the effects of L-NAME, 7-NI and L-NIL on carrageenan-induced hindpaw oedema and NOS activity, British Journal of Pharmacology, 1998, pp. 1119-1126, vol. 123.

Michael G. Osborne et al., Effects of intrathecal administration of nitric oxide synthase inhibitors on carrageenan-induced thermal hyperalgesia, British Journal of Pharmacology, 1999, pp. 1840-1846, vol. 126.

Gila Moalem et al., Immune and inflammatory mechanisms in neuropathic pain, Brain Research Reviews, 2006, pp. 240-264, vol. 51.

N. Fusetani et al., Astrogorgiadiol and Astrogorgin, Inhibitors of Cell Division in Fertilized Starfish Eggs, from a Gorgonian Astrogoria Sp., Tetrahedron Letters, 1989, pp. 7079-7082, vol. 30, No. 50, Great Britain.

Koji Yamada et al., Bioactive Terpenoids from Octocorallia. 3. A New Eunicellin-Based Diterpenoid from the Soft Coral cladiella sphaeroides, Journal of Natural Products, 1997, pp. 393-396, vol. 60, No. 4.

Atallah F. Ahmed et al., Eunicellin-Based Diterpenoids, Australins A-D, Isolated from the Soft Coral Cladiella australis, Journal of Natural Products, 2005, pp. 1051-1055, vol. 68, No. 7.

Claudia A. Ospina et al., Bioactive Compounds from the Gorgonian Briareum polyanthes. Correction of the Structures of Four Asbestinane-Type Diterpenes, Journal of Natural Products, 2006, pp. 1721-1727, vol. 69, No. 12.

Maria J. Ortega et al., A New Cladiellane Diterpenoid from *Eunicella labiata*, Journal of Natural Products, 1997, pp. 485-487, vol. 60, No. 5.

Tomofumi Miyamoto et al., Bioactive Terpenoids from Octocorallia, I. Bioactive Diterpenoids: Litophynols A and B from the Mucus of the Soft Coral Litophyton SP., Journal of Natural Products, Sep. 1994, pp. 1212-1219, vol. 57, No. 9.

Guey-Horng Wang et al., Pachyclavulariaenones A-C, three novel diterpenoids from the soft coral *Pachyclavularia violacea*, Tetrahedron Letters, 2001, pp. 2333-2336, vol. 42.

Perveen Sharma et al., Sclerophytins A and B. Isolation and Structures of Novel Cytotoxic Diterpenes from the Marine Coral *Sclerophytum capitalis*, J. Chem. So. Perkin Trans., 1988, pp. 2537-2540, vol. 1.

Salvatore Cuzzocrea et al., Effects of Combination M40403 and Dexamethasone Therapy on Join Disease in a Rat Model of Collagen-Induced Arthritis, Arthrities & Rheumatism, Jun. 2005, pp. 1929-1940, vol. 52, No. 6.

Thomas P. Misko et al., Mediation of inflammation by encephalitogenic cells: interferon γ induction of nitric oxide synthase and cyclooxygenase 2, Journal of Neuroimmunology, 1995, pp. 195-204, vol. 61.

Masaki Toriyabe et al., Contribution of Interaction between Nitric Oxide and Cyclooxygenases to the Production of Prostaglandins in Carrageenan-induced Inflammation, Anesthesiology, Oct. 2004, pp. 983-990, vol. 101, No. 4.

Ruben Lopez-Vales et al., Effects of COX-2 and iNOS Inhibitors Alone or in Combination with Olfactory Ensheathing Cell Grafts after Spinal Cord Injury, Spine, 2006, pp. 1100-1106, vol. 31, No. 10.

* cited by examiner

COMPOUNDS FROM SOFT CORAL, METHOD OF PREPARATION AND PHARMACEUTICAL USES THEREOF

BACKGROUND OF THE INVENTION

1. Field of the Invention

The invention relates to novel compounds from a soft coral. Said compounds from the soft coral have ability to inhibit the expression of inducible nitric oxide synthase (iNOS) and/or cyclooxygenase-2 (COX-2).

2. Description of the Related Art

With the progression of civilization, we human beings not only have longevity, but also emphasize the quality of our daily lives. However, a specific and effective drug is still absent for many diseases nowadays, such as cancer, chronic pain and atherosclerosis.

Inflammation has been proven to play an important role in the occurrence of several diseases in many studies. The occurrence of the inflammation-related diseases is highly associated with chronic and long-term inflammation induced by free radicals, pollution, food, ages, and pressure.

Atherosclerosis leads to remold a blood vessel and further causes the reduction of the inside diameter of the vessel. Therefore, it is an important risk factor of one of the leading causes of death, acute and lethal cardiovascular diseases, such as myocardial infarction, stroke and peripheral vascular diseases (Libby, Am J Clin Nutr 83:456S-460S, 2006). Atherosclerosis is proven to be a chronic inflammatory cardiovascular disease (Ross, N Engl J Med 340: 115-126, 1999). When intima cells of the blood vessel are pressed or injured, monocytes are induced to differentiate into macrophages and accumulate abundantly around the injured tissue. Through a series of inflammatory reactions, smooth muscle cells of the blood vessel proliferate and inflammatory cells accumulate, and such reactions damage the blood flow and lead to cardiovascular diseases finally (Lucas and Greaves, Exp Rev Mol Med 3:1-18, 2001; Gordon, Bioassays 17:977-986, 1995;). In animal model studies, the inflammatory critical factors of inducible nitric oxide synthase and cyclooxygenase-2 are shown to play an important role in atherosclerosis (Cipollone, Lupus 14:756-759, 2005; Boyle, Curr Vasc Pharmacol 3:63-68, 2005). Furthermore, bulk of inducible nitric oxide synthase and cyclooxygenase-2 is expressed in the human atherosclerosis tissue that comprises macrophages and proliferated smooth muscle cells (Baker et al, Arterioscler Thromb Vasc Biol 19:646-655, 1999; Buttery et al, Lab Invest 75:77-85, 1996). Presently, inducible nitric oxide synthase and cyclooxygenase-2 inhibitors are proven to significantly prevent the occurrence of atherosclerosis (Burleigh et al, Circulation 105:1816-23, 2002; Hayashi et al, Atherosclerosis 187:316-324, 2006; Osiecki, Altern Med Rev. 9: 32-53, 2004).

According to the definition made by International Association for the Study of Pain (IASP), pain is an unpleasant sensory and emotional experience associated with actual or potential tissue damage, or described in terms of such damage. With the extension of longevity, the opportunities and duration of pain are raised. To estimate in the conservative way, the global anodyne consumption reaches around one hundred billion US dollars. Improving life quality through pain control is an important subject. Among various pains, the factors of neuropathic pain are diverse, such as reduced distal circulation due to diabetes mellitus, neuron damage due to amputation or injury, viral infection and unknown reasons. Clinically, anodynes are divided into addictive anodynes and non-addictive anodynes. The addictive anodyne mainly comprises opiate, but the effect thereof to neuropathic pain is not satisfactory. The non-addictive anodyne comprises a steroid type and a non-steroid type. The steroid anodyne relives pain mainly through an anti-inflammatory pathway. However, the steroid anodyne is nonspecific, and the side effects are significant. The long-term usage is prohibited. On the other hand, the non-steroid anodyne comprises a pain-relieving type (such as panadol) and an anti-inflammatory type (such as aspirin). A non-steroid anti-inflammatory drug (NSAID) is now known to be safe with fewer side effects. The mechanism of a specific NSAID is through inhibiting inducible nitric oxide synthase and cyclooxygenase-2 pathways to relieve pain (Turini and DuBois, Annual Rev Med 53:35, 2002; Handy et al, Br J Pharmacol 123:1119-1126, 1998; Osborne et al, Br J Pharmacol 126:1840-1846, 1999). The product of NO or PGE2 catalyzed by inducible nitric oxide synthase or cyclooxygenase-2 is shown to be critical to the occurrence, maintenance and sensitivity of pain in the central neural system and periphery tissues (Moalem and Tracey, Brain Res Rev 51:240-264, 2006). Compared to using nerve blockers for pain relieving, administering inducible nitric oxide synthase and cyclooxygenase-2 inhibitors does not affect movement and neuron. Therefore, it is an important aspect for drug development.

Recently, many eunicellin-type compounds with a bioactivity had been isolated from the soft corals, such as spp. of *Astrogorgia* (Fusetani et al., Tetrahedron Lett., 30:7079-7082, 1989), *Cladiella* (Yamada et al., J. Nat. Prod., 60:393-396, 1997; Ahmed et al., J. Nat. Prod., 68:1051-1055, 2005), *Briareum* (Ospina and Rodriguez, J. Nat. Prod., 69:1721-1727, 2006), *Eunicella* (Ortega et al., J. Nat. Prod., 60:485-487, 1997), *Litophyton* (Miyamoto et al., J. Nat. Prod., 57:1212-1219, 1994), *Pachyclavularia* (Wang et al., Tetrahedron Lett., 42:2333-2336, 2001), *Sclerophytum* (Sharma and Alam, J. Chem. Soc., Perkin Trans. 1, 2537-2540, 1988). Soft coral is a possible resource of novel compounds.

SUMMARY OF THE INVENTION

One object of the invention is to provide novel compounds from the soft coral. Said compounds can be isolated from a cultured soft coral and can significantly inhibit the functions of inflammatory proteins in vitro. Thus, the compounds are shown to be able to treat a disease associated with inducible nitric oxide synthase and/or cyclooxygenase-2.

Another object of the invention is to provide an extract of *Klyxum simplex* comprising the compound mentioned above.

Another object of the invention is to provide a method for preparing the compound from the soft coral mentioned above.

Still another object of the invention is to provide a method for inhibiting inducible nitric oxide synthase and/or cyclooxygenase-2 comprising administering a subject with said compound from the soft coral or the extract.

Yet still another object of the invention is to provide a method for treating a disease associated with inducible nitric oxide synthase and/or cyclooxygenase-2 comprising administering a subject with said sulfur-containing compound or the extract.

DETAILED DESCRIPTION OF THE INVENTION

Figure 1:
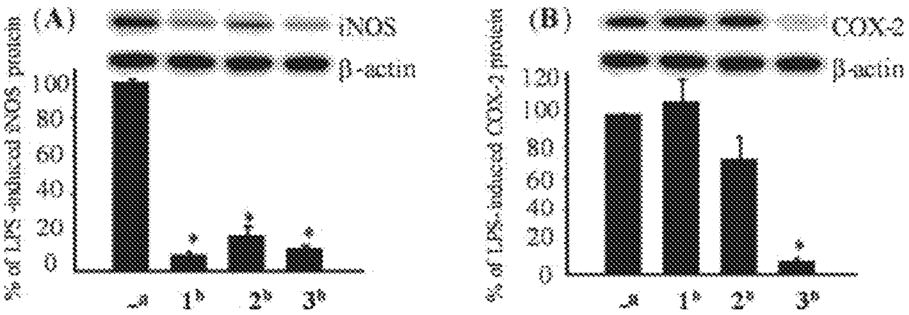
FIG. 1 shows the effect of the compounds represented by formulae 2-4 on iNOS and COX-2 protein expression of RAW264.7 macrophage cells by immunoblot analysis. (A) Immunoblots of iNOS and β-actin; (B) Immunoblots of COX-2 and β-actin. The values are mean±SEM. (n=6). Relative intensity of the LPS alone stimulated group was taken as 100%. Under the same experimental condition CAPE (caffeic acid phenylethyl ester, 10 μM) reduced the levels of the iNOS and COX-2 to 2.5±3.7% and 67.2±13.4%, respectively. *Significantly different from LPS alone stimulated group (*P<0.05). [a]stimulated with LPS, [b]stimulated with LPS in the presence of the compounds represented by formulae 2-4 (10 μM).

The applicants isolate novel eunicellin compounds with a bioactivity from *Klyxum simplex*.

The compound according to the invention is represented by the following general formula 1, formula 1

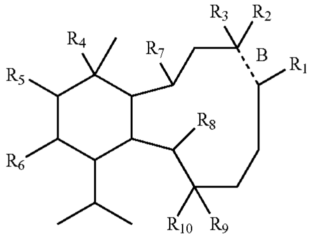

wherein:

$R_1$ is selected from the group consisting of —H, —OH, —OC(═O)$R_{11}$, —OOH, and OAc;

$R_2$ is selected from the group consisting of —S(C═O)$CH_3$ and —OH;

$R_3$ is selected from the group consisting of —$CH_3$ and —OH;

$R_4$ is selected from the group consisting of —OH and —OAc;

$R_5$ is selected from the group consisting of —H, —OAc, and —OC(═O)$CH_2CH_2CH_3$;

$R_6$ is selected from the group consisting of —H, —OC(═O)$CH_2CH_2CH_3$, —OC(═O)$CH_2CH_2$S(═O)$CH_3$, and —OAc;

$R_7$ is selected from the group consisting of —H, —OAc, and ═O;

$R_8$ is —H;

$R_9$ is —OC(═O)$CH_2CH_2CH_3$;

$R_{10}$ is —$CH_3$;

$R_{11}$ is an alkyl group; and

B is a single bond; or $R_1$ and $R_2$ together form the group consisting of —O— and a double bond; or $R_2$ and $R_3$ together form ═$CH_2$; or $R_7$ and $R_8$ together form —O—; or $R_8$ and $R_9$ together form a double bond; or $R_1$ and $R_8$ together form —O—; or $R_9$ and $R_{10}$ together form ═$CH_2$; or $R_2$ and $R_8$ together form a single bond; or $R_2$ and B together form ═O and $R_1$ and B together form ═O;

wherein the compound is not the compound represented by the following formula 17 or 18;

formula 17

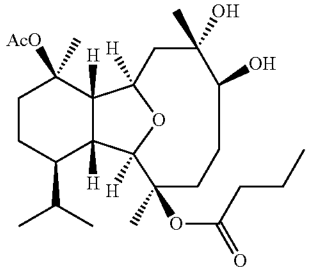

;

formula 18

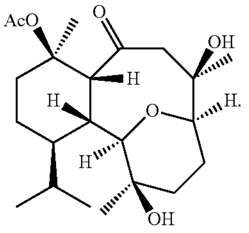

Preferably, $R_7$ and $R_8$ together form —O—.

Preferably, B is a single bond.

Preferably, $R_{11}$ is an alkyl group having 13 to 17 carbon atoms.

According to the preferred embodiments of the invention, the compound represented by general formula 1 is represented by one of the following formulae 2 to 16, formula 2

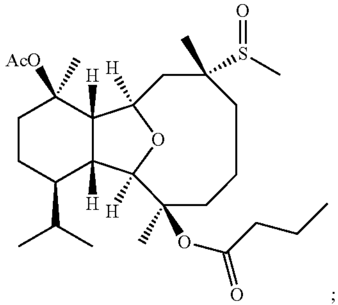

;

formula 3

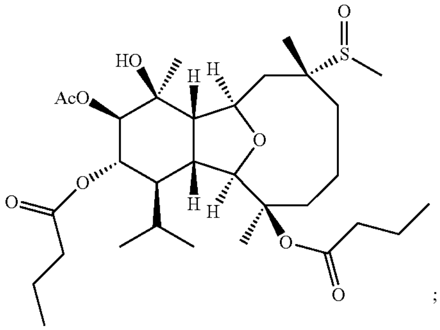

;

-continued
formula 4
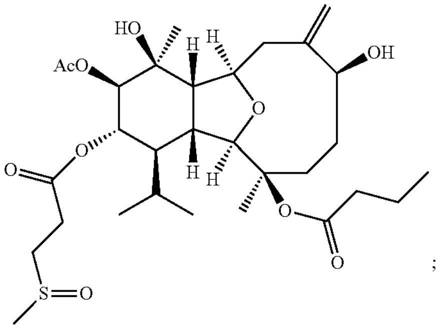
;
formula 5
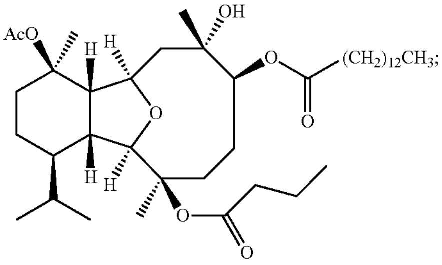
formula 6
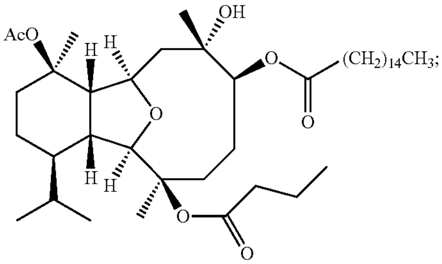
formula 7
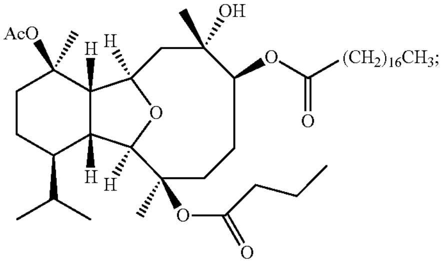
formula 8
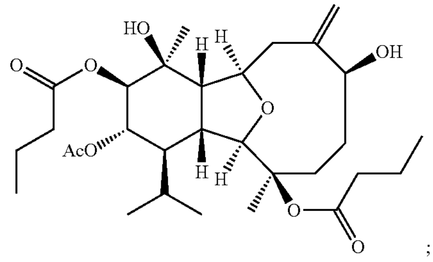
;
-continued
formula 9
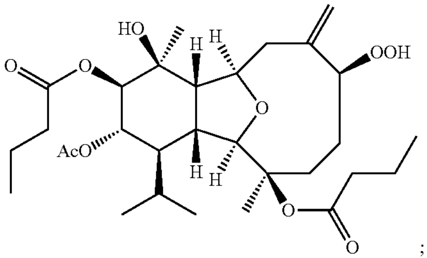
;
formula 10
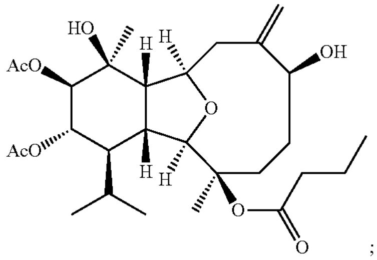
;
formula 11
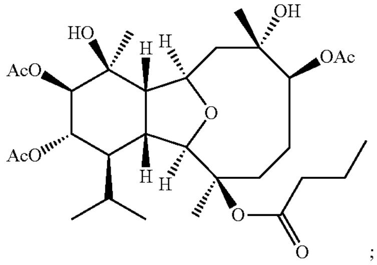
;
formula 12
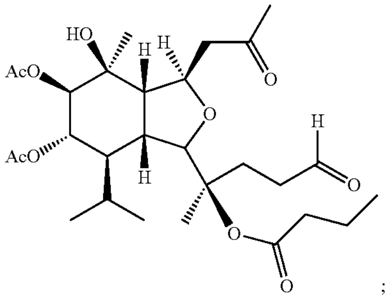
;
formula 13
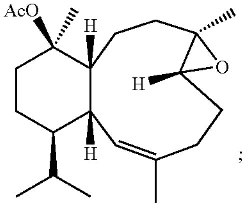
;
formula 14
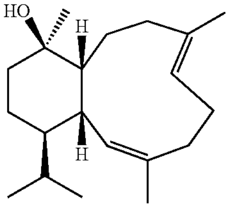
;

-continued formula 15

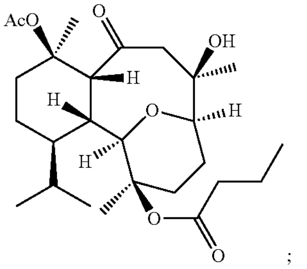

;

formula 16

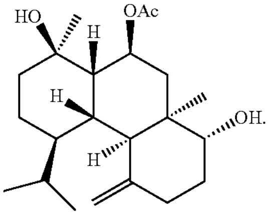

In one preferred embodiment of the invention, the compound represented by general formula 1 is provided in an extract of *Klyxum simplex*. Therefore, the invention provides an extract of *Klyxum simplex* comprising the compound represented by general formula 1. Preferably, *Klyxum simplex* is cultured. The process for preparing the extract is described below.

The invention also provides a method for preparing the compound represented by general formula 1 comprising obtaining the compound from an extract of *Klyxum simplex*. Preferably, *Klyxum simplex* is cultured to avoid collecting the wild organisms in the ocean and to cause ecological damage.

In one preferred embodiment of the invention, the extract is prepared by a process comprising steps of:

(a) mincing *Klyxum simplex*; and (b) extracting the minced *Klyxum simplex* with an organic solvent.

Preferably, the organic solvent is selected from the group consisting of an alcohol, an ester, a ketone, an ether, chloroform, dichloromethane, and benzene.

In another aspect, *Klyxum simplex* is preferred freeze-dried before step (a).

In one preferred embodiment of the invention, the cultured octocoral was collected and freeze-dried. The freeze-dried material was minced and extracted exhaustively with EtOH. The EtOH extract of the frozen organism was partitioned between $CH_2Cl_2$ and $H_2O$. The $CH_2Cl_2$-soluble portion was subjected to column chromatography on silica gel and eluted with EtOAc in n-hexane (0-100% of EtOAc, gradient) and then further with MeOH in EtOAc with increasing polarity to yield 40 fractions. Fraction 37, eluted with EtOAc-MeOH (3:1), was rechromatographed over a Sephadex® LH-20 column using MeOH as the mobile phase to afford five subfractions (A1-A4). Subfraction A3 was separated by reversephase HPLC ($CH_3CN$—$H_2O$, 1:3 to 1:1) to afford compounds represented by the formulae 2 and 3. Fraction 38, eluted with EtOAc-MeOH (2:1), was rechromatographed over a Sephadex LH-20 column using MeOH as the mobile phase to afford five subfractions (B1-B5). Subfraction B2 was separated by reverse-phase HPLC ($CH_3CN$—$H_2O$, 1:3 to 1:1) to afford compound represented by the formula 4. Fraction 10, eluted with n-hexane-EtOAc (15:1), was rechromatographed over a Sephadex LH-20 column, using acetone as the mobile phase to afford five subfractions (C1-C4). Subfraction C3 was separated by reversephase HPLC ($CH_3CN$—$H_2O$, 6:1 to 3:1) to afford compounds represented by formulae 13 and 14. Fraction 21, eluted with n-hexane-EtOAc (9:1), was rechromatographed over a Sephadex LH-20 column, using acetone as the mobile phase to afford five subfractions (D1-D5). Subfraction D3 was separated by reversephase HPLC ($CH_3CN$, 100%) to afford compounds represented by formulae 5, 6, and 7, respectively. Fraction 23, eluted with n-hexane-EtOAc (5:1), was rechromatographed over a Sephadex LH-20 column, using acetone as the mobile phase to afford five subfractions (E1-E5). Subfractions E3 and E4 were separated by reverse-phase HPLC ($CH_3CN$—$H_2O$, 4:1 to 1:1) to afford compounds represented by formulae 8, 9, 10, and 16, respectively. Fraction 26, eluted with n-hexane-EtOAc (2:1), was rechromatographed over a Sephadex LH-20 column, using acetone as the mobile phase to afford five subfractions (F1-F4). Subfraction F3 was separated by reverse-phase HPLC ($CH_3CN$—$H_2O$, 3:1 to 1:2) to afford compounds represented by formula 11, 12, and 15.

The present invention also provides a method for inhibiting inducible nitric oxide synthase and/or cyclooxygenase-2 comprising administering a subject with the compound represented by general formula 1.

The present invention also provides a method for inhibiting inducible nitric oxide synthase and/or cyclooxygenase-2 comprising administering a subject with the extract of *Klyxum simplex*.

The present invention further relates to a method for treating a disease associated with inducible nitric oxide synthase and/or cyclooxygenase-2 comprising administering a subject with the compound represented by the general formula 1.

The present invention further relates to a method for treating a disease associated with inducible nitric oxide synthase and/or cyclooxygenase-2 comprising administering a subject with the extract of *Klyxum simplex*.

Because the compound represented by general formula 1 and the extract of *Klyxum simplex* have ability to inhibit the accumulation of inducible nitric oxide synthase and/or cyclooxygenase-2, they are useful in treating the diseases associated with inducible nitric oxide synthase and/or cyclooxygenase-2. Many diseases have been reported to be related to the function of inducible nitric oxide synthase and/or cyclooxygenase-2, such as arthritis (Cuzzocrea et al, Arthritis Rheum. 52:1929-40, 2005), multiple sclerosis (Misko et al, J Neuroimmunol. 61:195-204, 1995), inflammatory pain (Toriyabe et al, Anesthesiology 101, 983-990, 2004), and spinal cord injury (Lopez-Vales et al, Spine. 31:1100-6, 2006). Therefore, the disease is preferably selected from the group consisting of inflammation, atherosclerosis, neuropathic pain, inflammatory neointimal proliferation, arthritis, multiple sclerosis, inflammatory pain, and spinal cord injury. As illustrated in Example, the compounds represented by formulae 2, 3 and 4 significantly lowered the expression of inducible nitric oxide synthase of macrophage cells stimulated with LPS. Furthermore, the compounds represented by formula 4 significantly lowered the expression of cyclooxygenase-2 of macrophage cells stimulated with LPS. In one preferred embodiment of the invention, administering the compound represented by general formula 1 through intrathecal injection is effective in treating neuropathic pain. Compounds represented by formulae 5-16, in particular 6-10, 14, and 15 were found to significantly reduce the expression of iNOS protein, relative to the control cells stimulated with LPS only. Furthermore, compounds represented by formulae 14-15 also could effectively reduce COX-2 expression in the same macrophage cells with LPS treatment.

The compound represented by general formula 1 can be administered orally or through injection. Preferably, the compound is administered by injection.

The following examples are given for the purpose of illustration only and are not intended to limit the scope of the present invention.

EXAMPLE

General Experimental Procedures

Melting points were determined using a Fisher-Johns melting point apparatus. Optical rotations were measured on a JASCO P-1020 polarimeter. IR spectra were recorded on a JASCO FT/IR-4100 infrared spectrophotometer. ESIMS were obtained with a Bruker APEX II mass spectrometer. LC-ESI MS/MS spectrometry analysis was carried out using an Applied Biosystem API 4000 tandem quadrupole mass spectrometer. NMR spectra were recorded on a Varian Unity INOVA 500 FT-NMR at 500 MHz for $^{1}H$ and 125 MHz for $^{13}C$ or on a Varian 400 MR FT-NMR at 400 MHz for $^{1}H$ and 100 MHz for $^{13}C$, or on a Bruker AVANCEDPX 300 FT-NMR at 300 MHz for $^{1}H$ and 75 MHz for $^{13}C$, respectively. Silica gel (Merck, 230-400 mesh) was used for column chromatography. Precoated silica gel plates (Merck, Kieselgel 60 F-254, 0.2 mm) were used for analytical TLC. High performance liquid chromatography was performed on a Hitachi L-7100 HPLC apparatus with a ODS column (250×21.2 mm, 5 mm).

Extraction and Isolation

Specimens of the cultured soft coral *K. simplex* were collected by hand in a 30 ton cultivating tank located in the National Museum of Marine Biology and Aquarium, Taiwan, in July 2005. A voucher sample (CSC-2) was deposited at the Department of Marine Biotechnology and Resources, National Sun Yat-sen University. The cultured octocoral (1.5 kg fresh wt) was collected and freeze-dried. The freeze-dried material was minced and extracted exhaustively with EtOH (3×10 L). The EtOH extract of the frozen organism was partitioned between $CH_2Cl_2$ and $H_2O$. The $CH_2Cl_2$-soluble portion (15.2 g) was subjected to column chromatography on silica gel and eluted with EtOAc in n-hexane (0-100% of EtOAc, gradient) and then further with MeOH in EtOAc with increasing polarity to yield 40 fractions. Fraction 37, eluted with EtOAc-MeOH (3:1), was rechromatographed over a Sephadex® LH-20 column using MeOH as the mobile phase to afford five subfractions (A1-A4). Subfraction A3 was separated by reversephase HPLC ($CH_3CN—H_2O$, 1:3 to 1:1) to afford compounds represented by the formulae 2 (2.0 mg) and 3 (2.2 mg). Fraction 38, eluted with EtOAc-MeOH (2:1), was rechromatographed over a Sephadex LH-20 column using MeOH as the mobile phase to afford five subfractions (B1-B5). Subfraction B2 was separated by reverse-phase HPLC ($CH_3CN—H_2O$, 1:3 to 1:1) to afford compound represented by the formula 4 (1.0 mg). Fraction 10, eluted with n-hexane-EtOAc (15:1), was rechromatographed over a Sephadex LH-20 column, using acetone as the mobile phase to afford five subfractions (C1-C4). Subfraction C3 was separated by reversephase HPLC ($CH_3CN—H_2O$, 6:1 to 3:1) to afford compounds represented by formulae 13 (6.0 mg) and 14 (2.2 mg). Fraction 21, eluted with n-hexane-EtOAc (9:1), was rechromatographed over a Sephadex LH-20 column, using acetone as the mobile phase to afford five subfractions (D1-D5). Subfraction D3 was separated by reversephase HPLC ($CH_3CN$, 100%) to afford compounds represented by formulae 5 (15.5 mg), 6 (4.2 mg), and 7 (1.1 mg), respectively. Fraction 23, eluted with n-hexane-EtOAc (5:1), was rechromatographed over a Sephadex LH-20 column, using acetone as the mobile phase to afford five subfractions (E1-E5). Subfractions E3 and E4 were separated by reverse-phase HPLC ($CH_3CN—H_2O$, 4:1 to 1:1) to afford compounds represented by formulae 8 (1.2 mg), 9 (1.1 mg), 10 (1.0 mg), and 16 (1.1 mg), respectively. Fraction 26, eluted with n-hexane-EtOAc (2:1), was rechromatographed over a Sephadex LH-20 column, using acetone as the mobile phase to afford five subfractions (F1-F4). Subfraction F3 was separated by reverse-phase HPLC ($CH_3CN—H_2O$, 3:1 to 1:2) to afford compounds represented by formula 11 (15.3 mg), 12 (1.2 mg), and 15 (2.3 mg).

Compound represented by formula 2. Colorless oil; $[\alpha]^{25}_{D}$−33 (c 0.20, $CHCl_3$); IR (neat) $\nu_{max}$ 1738 and 1053 $cm^{-1}$; $^{13}C$ and $^{1}H$-NMR data (400 MHz; $CHCl_3$), see Table 1; ESIMS m/z 521 $[M+Na]^+$; HRESIMS m/z 521.2917 $[M+Na]^+$ (calcd. 521.1913 for $C_{27}H_{46}O_6SNa$).

TABLE 1

$^{1}H$ and $^{13}C$ NMR chemical shifts for compound represented by formula 2

| C | $^{1}H^{a}$ (ppm) | $^{13}C^{b}$ (ppm) |
|---|---|---|
| 1 | 2.16 (dd, 11.6, 7.2)[c] | 42.3 (CH)[b] |
| 2 | 3.53 (s) | 92.0 (CH) |
| 3 | — | 86.7 (qC) |
| 4 | 2.64 (dd, 14.4, 8.0); 1.65, m | 38.4 ($CH_2$) |
| 5 | 1.84 (m); 1.04 (m) | 17.4 ($CH_2$) |
| 6 | 2.50 (dd, 11.2, 6.0) 1.85 (m) | 34.5 ($CH_2$) |
| 7 | — | 59.3 (qC) |
| 8 | 2.15 (dd, 15.2, 3.6); 1.71 (d, 14.8) | 42.2 ($CH_2$) |
| 9 | 3.96 (ddd, 14.8, 7.6, 3.2) | 76.1 (CH) |
| 10 | 3.13 (br t, 8.0) | 53.8 (CH) |
| 11 | — | 81.8 (qC) |
| 12 | 2.14 (m); 1.34 (m) | 32.4 ($CH_2$) |
| 13 | 1.41 (m); 1.35 (m) | 17.4 ($CH_2$) |
| 14 | 1.19 (m) | 42.3 (CH) |
| 15 | 1.38 (s) | 23.2 ($CH_3$) |
| 16 | 1.08 (s) | 20.1 ($CH_3$) |
| 17 | 1.46 (s) | 25.0 ($CH_3$) |
| 18 | 1.76 (m) | 28.9 (CH) |
| 19 | 0.95 (d, 6.8) | 21.6 ($CH_3$) |
| 20 | 0.81 (d, 6.8) | 15.1 ($CH_3$) |
| 3-n-butyrate | 1.01 (t, 7.2) | 13.7 ($CH_3$) |
| | 1.76 (m) | 18.7 ($CH_2$) |
| | 2.35 (m) | 37.3 ($CH_2$) |
| | | 172.6 (qC) |
| 11-OAc | 2.00 (s) | 22.5 ($CH_3$) |
| | | 170.2 (qC) |
| 7-SOMe | 2.42 (s) | 32.0 ($CH_3$) |

[a]Spectrum recorded at 400 MHz in $CDCl_3$.
[b]100 MHz in $CDCl_3$.
[c]J values (in Hz) in parentheses.

Compound represented by formula 3. Colorless oil; $[\alpha]^{25}_{D}$−67 (c 0.22, $CHCl_3$); IR (neat) $\nu_{max}$3452, 1734 and 1052 $cm^{-1}$; 1 $^{13}C$ and $^{1}H$ NMR data (400 MHz; $CHCl_3$), see Table 2; ESIMS m/z 623 $[M+Na]^+$; HRESIMS m/z 623.3226 $[M+Na]^+$ (calcd. 623.3230 for $C_{31}H_{52}O_9Na$).

TABLE 2

$^{1}H$ and $^{13}C$ NMR chemical shifts for compound represented by formula 3

| C | $^{1}H^{a}$ (ppm) | $^{13}C^{b}$ (ppm) |
|---|---|---|
| 1 | 2.41 (dd, 11.6, 7.2)[c] | 43.5 (CH)[b] |
| 2 | 3.53 (s) | 92.6 (CH) |
| 3 | — | 86.3 (qC) |
| 4 | 2.64 (dd, 14.8, 6.8); 1.66 (m) | 38.9 ($CH_2$) |
| 5 | 1.89 (m); 1.04 (m) | 18.6 ($CH_2$) |
| 6 | 2.50 (dd, 12.0, 7.2); 1.87 (m) | 35.5 ($CH_2$) |
| 7 | — | 59.5 (qC) |

TABLE 2-continued

| $^1H$ and $^{13}C$ NMR chemical shifts for compound represented by formula 3 | | |
|---|---|---|
| C | $^1H^a$ (ppm) | $^{13}C^b$ (ppm) |
| 8 | 2.09 (dd, 15.2, 3.2); 1.62 (d, 14.4) | 42.3 ($CH_2$) |
| 9 | 4.10 (ddd, 14.4, 7.6, 3.2) | 76.0 (CH) |
| 10 | 2.59 (br t, 7.6) | 58.1 (CH) |
| 11 | — | 72.6 (qC) |
| 12 | 4.97 (d, 9.6) | 77.2 (CH) |
| 13 | 5.49 (dd, 11.2, 10.0) | 70.2 (CH) |
| 14 | 1.76 (m) | 47.6 (CH) |
| 15 | 1.40 (s) | 24.3 ($CH_3$) |
| 16 | 1.09 (s) | 20.7 ($CH_3$) |
| 17 | 1.07 (s) | 26.8 ($CH_3$) |
| 18 | 1.72 (m) | 30.9 (CH) |
| 19 | 0.96 (d, 7.2) | 24.3 ($CH_3$) |
| 20 | 1.01 (d, 7.2) | 17.1 ($CH_3$) |
| 3-n-Bubyrate | 0.99 (t, 7.6) | 15.0 ($CH_3$) |
| | 1.69 (m) | 19.4 ($CH_2$) |
| | 2.39 (m); 2.31 (m) | 38.1 ($CH_2$) |
| | | 171.1 (qC) |
| 12-OAc | 2.08 (s) | 21.8 ($CH_3$) |
| | | 168.4 (qC) |
| 13-n-Bubyrate | 0.95 (t, 7.6) | 14.0 ($CH_3$) |
| | 1.60 (m) | 19.2 ($CH_2$) |
| | 2.21 (m) | 37.3 ($CH_2$) |
| | | 170.4 (qC) |
| 7-SOMe | 2.42 (s) | 32.8 ($CH_3$) |

[a]Spectrum recorded at 400 MHz in $CDCl_3$.
[b]100 MHz in $CDCl_3$.
[c]J values (in Hz) in parentheses.

Compound represented by formula 4. Colorless oil; $[\alpha]^{25}_D$–84 (c 0.10, $CHCl_3$); IR (neat) $\nu_{max}$ 3478, 1735 and 1054 $cm^{-1}$; $^{13}C$ and $^1H$ NMR data (400 MHz; $CDCl_3$), see Table 3; ESIMS m/z 623 $[M+Na]^+$; HRESIMS m/z 623.2863 $[M+Na]^+$ (calcd 623.2867 for $C_{30}H_{48}O_{10}SNa$).

TABLE 3

| $^1H$ and $^{13}C$ NMR chemical shifts for compound represented by formula 4 | | |
|---|---|---|
| C | $^1H^a$ (ppm) | $^{13}C^b$ (ppm) |
| 1 | 2.56 (dd, 11.6, 7.6)[c] | 42.3 (CH)[b] |
| 2 | 3.60 (s) | 90.9 (CH) |
| 3 | — | 84.1 (qC) |
| 4 | 2.25 (m); 1.71 (m) | 30.6 ($CH_2$) |
| 5 | 2.15 (m); 1.74 (m) | 35.9 ($CH_2$) |
| 6 | 4.32 (dd, 10.4, 4.0) | 72.7 (CH) |
| 7 | — | 148.7 (qC) |
| 8 | 2.87 (dd, 14.8, 4.4); 2.44 (d, 14.0) | 41.5 ($CH_2$) |
| 9 | 4.30 (ddd, 14.0, 10.4, 4.4) | 78.7 (CH) |
| 10 | 2.67 (dd, 10.8, 8.0) | 49.8 (CH) |
| 11 | — | 72.9 (qC) |
| 12 | 5.04 (d, 9.6) | 76.6 (CH) |
| 13 | 5.55 (dd, 10.8, 9.6) | 72.2 (CH) |
| 14 | 1.77 (m) | 48.2 (CH) |
| 15 | 1.60 (s) | 23.3 ($CH_3$) |
| 16 | 5.46 (s); 5.12 (s) | 116.3 ($CH_2$) |
| 17 | 1.19 (s) | 27.1 ($CH_3$) |
| 18 | 2.01 (m) | 28.9 (CH) |
| 19 | 0.99 (d, 7.2) | 24.7 ($CH_3$) |
| 20 | 0.93 (d, 7.2) | 16.9 ($CH_3$) |
| 3-n-Butyrate | 0.92 (t, 7.2) | 14.7 ($CH_3$) |
| | 1.56 (m) | 19.5 ($CH_2$) |
| | 2.12 (m) | 38.1 ($CH_2$) |
| | | 170.7 (qC) |
| 12-OAc | 2.13 (s) | 21.7 ($CH_3$) |
| | | 168.6 (qC) |

TABLE 3-continued

| $^1H$ and $^{13}C$ NMR chemical shifts for compound represented by formula 4 | | |
|---|---|---|
| C | $^1H^a$ (ppm) | $^{13}C^b$ (ppm) |
| 13-Methylsulfoxyl-propiorate | 2.62 (s) | 39.7 ($CH_3$) |
| | 2.83 (m); 2.80 (m) | 28.3 ($CH_2$) |
| | 3.05 (m) | 49.4 ($CH_2$) |
| | | 168.9 (qC) |

[a]Spectrum recorded at 400 MHz in $CDCl_3$.
[b]100 MHz in $CDCl_3$.
[c]J values (in Hz) in parentheses.

Compound represented by formula 5. Colorless oil; $[\ ]^{22}_D$–38 (c 1.55, $CHCl_3$); IR (neat) $\nu_{max}$ 3460, 1738 $cm^{-1}$; $^{13}C$ and $^1H$ NMR data (400 MHz; $CHCl_3$), see Tables 4 and 6; ESIMS m/z 701 $[M+Na]^+$; HRESIMS m/z 701.4974 $[M+Na]^+$ (calcd for $C_{40}H_{70}O_8Na$, 701.4968).

Compound represented by formula 6. Colorless oil; $[\ ]^{22}_D$–40 (c 0.42, $CHCl_3$); IR (neat) $\nu_{max}$ 3463, 1723 $cm^{-1}$; $^{13}C$ and $^1H$ NMR data (400 MHz; $CHCl_3$), see Tables 4 and 6; ESIMS m/z 730 $[M+Na]^+$; HRESIMS m/z 729.5277 $[M+Na]^+$ (calcd for $C_{42}H_{74}O_8Na$, 729.5281).

Compound represented by formula 7. Colorless oil; $[\ ]^{22}_D$–38 (c 0.11, $CHCl_3$); IR (neat) $\nu_{max}$ 3437, 1734 $cm^{-1}$; $^{13}C$ and $^1H$ NMR data (400 MHz; $CDCl_3$), see Tables 4 and 6; ESIMS m/z 757.55 $[M+Na]^+$; HRESIMS m/z 757.5590 $[M+Na]^+$ (calcd for $C_{44}H_{78}O_8Na$, 757.5594).

Compound represented by formula 8. Colorless oil; $[\ ]^{22}_D$–64 (c 0.12, $CHCl_3$); IR (neat) $\nu_{max}$ 3452, 1734 $cm^{-1}$; $^{13}C$ and $^1H$ NMR data (400 MHz; $CDCl_3$), see Tables 4 and 6; ESIMS m/z 575 $[M+Na]^+$; HRESIMS m/z 575.3193 $[M+Na]^+$ (calcd for $C_{30}H_{48}O_9Na$, 575.3196).

Compound represented by formula 9. Colorless oil; $[\ ]^{22}_D$–74 (c 0.11, $CHCl_3$); IR (neat) $\nu_{max}$ 3452, 1738 $cm^{-1}$; $^{13}C$ and $^1H$ NMR data (500 MHz; $CDCl_3$), see Tables 4 and 6; ESIMS m/z 591 $[M+Na]^+$; HRESIMS m/z 591.3146 $[M+Na]^+$ (calcd for $C_{30}H_{48}O_{10}Na$, 591.3145).

Compound represented by formula 10. Colorless oil; $[\ ]^{22}_D$–53 (c 0.10, $CHCl_3$); IR (neat) $\nu_{max}$ 3467, 1738 $cm^{-1}$; $^{13}C$ and $^1H$ NMR data (500 MHz; $CDCl_3$), see Tables 4 and 7; ESIMS m/z 547 $[M+Na]^+$; HRESIMS m/z 547.2885 $[M+Na]^+$ (calcd for $C_{28}H_{44}O_9Na$, 547.2883).

Compound represented by formula 11. Colorless oil; $[\ ]^{22}_D$–27 (c 1.53, $CHCl_3$); IR (neat) $\nu_{max}$ 3478, 1734 $cm^{-1}$; $^{13}C$ and $^1H$ NMR data (300 MHz; $CDCl_3$), see Tables 4 and 7; ESIMS m/z 607 $[M+Na]^+$; HRESIMS m/z 607.3095 $[M+Na]^+$ (calcd for $C_{30}H_{48}O_{11}Na$, 607.3094).

Compound represented by formula 12. Colorless oil; $[\ ]^{22}_D$–23 (c 0.12, $CHCl_3$); IR (neat) $\nu_{max}$ 3460, 1738 and 1711 $cm^{-1}$; $^{13}C$ and $^1H$ NMR data (500 MHz; $CDCl_3$), see Tables 4 and 7; ESIMS m/z 563 $[M+Na]^+$; HRESIMS m/z 563.2833 $[M+Na]^+$ (calcd for $C_{28}H_{44}O_{10}Na$, 563.2832).

Compound represented by formula 13. Colorless oil; $[\ ]^{22}_D$–56 (c 0.60, $CHCl_3$); IR (neat) $\nu_{max}$ 1734 $cm^{-1}$; $^{13}C$ and $^1H$ NMR data (400 MHz; $CDCl_3$), see Tables 5 and 7; ESIMS m/z 371 $[M+Na]^+$; HRESIMS m/z 371.2560 $[M+Na]^+$ (calcd for $C_{22}H_{36}O_3Na$, 371.2562).

Compound represented by formula 14. Colorless oil; $[\ ]^{22}_D$–30 (c 0.22, $CHCl_3$); IR (neat) $\nu_{max}$ 3398 $cm^{-1}$; $^{13}C$ and $^1H$ NMR data (500 MHz; $CDCl_3$), see Tables 5 and 7; EIMS m/z 290 $[(5.9)M]^+$, 272 $[(9.9)M-H_2O]^+$, 257 $[(5.9)M-Me-H_2O]^+$; HREIMS m/z 290.2607 $[M]^+$ (calcd for $C_{20}H_{34}O$, 290.2610).

Compound represented by formula 15. Colorless oil; $[\ ]^{22}_D$–43 (c 0.23, $CHCl_3$); IR (neat) $\nu_{max}$ 3347 1731 and 1716 $cm^{-1}$; $^{13}C$ and $^1H$ NMR data (400 MHz; $CDCl_3$), see Tables 5 and 8; ESIMS m/z 489 $[M+Na]^+$; HRESIMS m/z 489.2831 $[M+Na]^+$ (calcd for $C_{26}H_{42}O_7Na$, 489.2828).

Compound represented by formula 16. Colorless oil; $[\ ]^{22}_{D}$−56 (c 0.11, $CHCl_3$); IR (neat) $\nu_{max}$ 3641 and 1735 $cm^{-1}$; $^{13}C$ and $^{1}H$ NMR data (400 MHz; $CDCl_3$), see Tables 5 and 8; ESIMS m/z 387 $[M+Na]^+$; HRESIMS m/z 387.2509 $[M+Na]^+$ (calcd for $C_{22}H_{36}O_4Na$, 387.2511).

TABLE 4

$^{13}C$ NMR Data for compounds represented by formulae 5-9.

| position | 5[a] | 6[a] | 7[a] | 8[a] | 9[b] |
|---|---|---|---|---|---|
| 1 | 42.3, CH [c] | 42.4, CH | 42.9, CH | 41.6, CH | 42.0, CH |
| 2 | 92.0, CH | 92.0, CH | 91.8, CH | 91.2, CH | 91.3, CH |
| 3 | 86.0, qC | 86.1, qC | 85.9, qC | 84.2, qC | 84.4, qC |
| 4 | 35.9, $CH_2$ | 36.0, $CH_2$ | 35.4, $CH_2$ | 29.7, $CH_2$ | 28.3, $CH_2$ |
| 5 | 29.1, $CH_2$ | 29.1, $CH_2$ | 29.8, $CH_2$ | 35.2, $CH_2$ | 29.9, $CH_2$ |
| 6 | 84.9, CH | 84.9, CH | 84.8, CH | 72.7, CH | 86.7, CH |
| 7 | 75.9, qC | 75.9, qC | 75.5, qC | 150.1, qC | 146.1, qC |
| 8 | 47.8, $CH_2$ | 47.8, $CH_2$ | 48.3, $CH_2$ | 40.9, $CH_2$ | 41.8, $CH_2$ |
| 9 | 75.5, CH | 75.5, CH | 75.5, CH | 78.7, CH | 78.8, CH |
| 10 | 52.8, CH | 52.8, CH | 53.2, CH | 49.2, CH | 49.5, CH |
| 11 | 82.2, qC | 82.2, qC | 82.1, qC | 72.8, qC | 72.8, qC |
| 12 | 32.0, $CH_2$ | 32.0, $CH_2$ | 32.7, $CH_2$ | 76.4, CH | 76.7, CH |
| 13 | 17.5, $CH_2$ | 17.5, $CH_2$ | 18.4, $CH_2$ | 70.9, CH | 71.2, CH |
| 14 | 42.4, CH | 42.4, CH | 43.0, CH | 47.7, CH | 47.7, CH |
| 15 | 22.9, $CH_3$ | 23.0, $CH_3$ | 23.8, $CH_3$ | 22.2, $CH_3$ | 22.6, $CH_3$ |
| 16 | 23.9, $CH_3$ | 23.9, $CH_3$ | 24.7, $CH_3$ | 117.0, $CH_2$ | 118.3, $CH_2$ |
| 17 | 24.8, $CH_3$ | 24.9, $CH_3$ | 25.7, $CH_3$ | 26.2, $CH_3$ | 26.6, $CH_3$ |
| 18 | 28.9, CH | 28.9, CH | 29.7, CH | 28.0, CH | 28.3, CH |
| 19 | 21.7, $CH_3$ | 21.7, $CH_3$ | 22.6, $CH_3$ | 23.6, $CH_3$ | 23.8, $CH_3$ |
| 20 | 15.2, $CH_3$ | 15.2, $CH_3$ | 16.1, $CH_3$ | 15.7, $CH_3$ | 15.9, $CH_3$ |
| 3-n- | 13.6, $CH_3$ | 13.6, $CH_3$ | 14.6, $CH_3$ | 13.7, $CH_3$ | 14.0, $CH_3$ |
| butyrate | 18.7, $CH_2$ | 18.7, $CH_2$ | 19.6, $CH_2$ | 18.4, $CH_2$ | 18.6, $CH_2$ |
| | 37.3, $CH_2$ | 37.3, $CH_2$ | 37.9, $CH_2$ | 35.9, $CH_2$ | 36.2, $CH_2$ |
| | 172.6, qC | 172.6, qC | 171.2, qC | 172.8, qC | 172.7, qC |
| 11-OAc | 22.5, $CH_3$ | 22.5, $CH_3$ | 23.3, $CH_3$ | | |
| | 170.1, qC | 170.1, qC | 168.7, qC | | |
| 12-n- | | | | 13.6, $CH_3$ | 13.8, $CH_3$ |
| butyrate | | | | 18.5, $CH_2$ | 18.7, $CH_2$ |
| | | | | 37.4, $CH_2$ | 37.6, $CH_2$ |
| | | | | 172.4, qC | 173.1, qC |
| 13-OAc | | | | 21.5, $CH_3$ | 21.7, $CH_3$ |
| | | | | 170.1, qC | 170.4, qC |
| 3' | 25.1, $CH_2$ | 25.1, $CH_2$ | 25.9, $CH_2$ | | |
| 2' | 34.7, $CH_2$ | 34.8, $CH_2$ | 35.4, $CH_2$ | | |
| 1' | 174.7, qC | 174.7, qC | 173.3, qC | | |
| 3" | 32.0 $CH_2$ | 31.9 $CH_2$ | 32.6 $CH_2$ | | |
| 2" | 22.7 $CH_2$ | 22.7 $CH_2$ | 23.5 $CH_2$ | | |
| 1" | 14.1, $CH_3$ | 14.1, $CH_3$ | 15.1, $CH_3$ | | |

[a]Spectra recorded at 100 MHz in $CDCl_3$ at 25° C.
[b]Spectra recorded at 125 MHz in $CDCl_3$ at 25° C.
[c]Multiplicities deduced by DEPT.

TABLE 5

$^{13}C$ NMR Data for compounds represented by formulae 10-16.

| position | 10[a] | 11[b] | 12[a] | 13[c] | 14[a] | | |
|---|---|---|---|---|---|---|---|
| 1 | 41.6, (CH)[d] | 43.0, (CH) | 42.2 (CH) | 36.7 (CH) | 36.8 (CH) | 50.1 (CH) | 31.4 (CH) |
| 2 | 91.1, (CH) | 93.0, (CH) | 88.5 (CH) | 129.6 (CH) | 130.6 (CH) | 78.0 (CH) | 51.7 (CH) |
| 3 | 84.3, (qC) | 85.9, (qC) | 84.4 (qC) | 133.8 (qC) | 133.4 (qC) | 81.0 (qC) | 144.9 (qC) |
| 4 | 29.7, ($CH_2$) | 35.9, ($CH_2$) | 27.8 ($CH_2$) | 29.0 ($CH_2$) | 32.3 ($CH_2$) | 28.5 ($CH_2$) | 30.4 ($CH_2$) |
| 5 | 35.2, ($CH_2$) | 29.2, ($CH_2$) | 39.4 ($CH_2$) | 26.1 ($CH_2$) | 25.8 ($CH_2$) | 21.5 ($CH_2$) | 32.2 ($CH_2$) |
| 6 | 72.6, (CH) | 84.8, (CH) | 201.4 (CH) | 64.9 (CH) | 124.6 (CH) | 80.3 (CH) | 69.8 (CH) |
| 7 | 150.0, (qC) | 75.8, (qC) | 206.3 (qC) | 60.9 (qC) | 138.3 (qC) | 85.3 (qC) | 38.9 (qC) |

TABLE 5-continued $^{13}C$ NMR Data for compounds represented by formulae 10-16.

| position | 10[a] | 11[b] | 12[a] | 13[c] | 14[a] | | |
|---|---|---|---|---|---|---|---|
| 8 | 40.9, ($CH_2$) | 47.6, ($CH_2$) | 50.7 ($CH_2$) | 39.4 ($CH_2$) | 39.9 ($CH_2$) | 50.0 ($CH_2$) | 36.2 ($CH_2$) |
| 9 | 78.7, (CH) | 75.6, (CH) | 75.4 (CH) | 23.5 ($CH_2$) | 24.0 ($CH_2$) | 209.0 (qC) | 70.3 (CH) |
| 10 | 49.2, (CH) | 56.6, (CH) | 53.9 (CH) | 42.5 (CH) | 47.0 (CH) | 56.2 (CH) | 46.6 (CH) |
| 11 | 72.8, (qC) | 72.7, (qC) | 72.0 (qC) | 85.8 (qC) | 73.5 (qC) | 83.3 (qC) | 71.4 (qC) |
| 12 | 75.7, (CH) | 76.7, (CH) | 77.0 (CH) | 32.3 ($CH_2$) | 36.1 ($CH_2$) | 31.3 ($CH_2$) | 38.6 ($CH_2$) |
| 13 | 71.0, (CH) | 70.7, (CH) | 70.9 (CH) | 19.9 ($CH_2$) | 20.4 ($CH_2$) | 20.3 ($CH_2$) | 21.1 ($CH_2$) |
| 14 | 47.6, (CH) | 47.3, (CH) | 46.1 (CH) | 42.9 (CH) | 45.6 (CH) | 37.2 (CH) | 40.9 (CH) |
| 15 | 22.2, ($CH_3$) | 23.2, ($CH_3$) | 21.4 ($CH_3$) | 25.8 ($CH_3$) | 25.0 ($CH_3$) | 24.5 ($CH_3$) | 111.9 ($CH_2$) |
| 16 | 117.0, ($CH_2$) | 23.8, ($CH_3$) | 30.6 ($CH_3$) | 19.2 ($CH_3$) | 17.0 ($CH_3$) | 23.9 ($CH_3$) | 23.2 ($CH_3$) |
| 17 | 26.1, ($CH_3$) | 25.8, ($CH_3$) | 26.1 ($CH_3$) | 23.8 ($CH_3$) | 26.1 ($CH_3$) | 25.2 ($CH_3$) | 28.5 ($CH_3$) |
| 18 | 28.0, (CH) | 30.2, (CH) | 28.7 (CH) | 27.5 (CH) | 26.5 (CH) | 28.5 (CH) | 26.8 (CH) |
| 19 | 23.6, ($CH_3$) | 23.4, ($CH_3$) | 23.6 ($CH_3$) | 22.7 ($CH_3$) | 22.1 ($CH_3$) | 22.6 ($CH_3$) | 22.8 ($CH_3$) |
| 20 | 15.7, ($CH_3$) | 16.1, ($CH_3$) | 15.4 ($CH_3$) | 16.6 ($CH_3$) | 18.5 ($CH_3$) | 14.9 ($CH_3$) | 21..8 ($CH_3$) |
| 3-n-butyrate | 13.6, ($CH_3$) | 13.7, ($CH_3$) | 13.7 ($CH_3$) | | | 15.6 ($CH_3$) | |
| | 18.5, ($CH_2$) | 18.4, ($CH_2$) | 18.4 ($CH_2$) | | | 19.6 ($CH_2$) | |
| | 37.3, ($CH_2$) | 37.4 ($CH_2$) | 37.4 ($CH_2$) | | | 37.9 ($CH_2$) | |
| | 172.4, (qC) | 172.3, (qC) | 172.6 (qC) | | | 171.1 (qC) | |
| 6-OAc | | 21.5, ($CH_3$) | | | | | |
| | | 172.1, (qC) | | | | | |
| 9-OAc | | | | | | | 22.7, ($CH_3$) |
| | | | | | | | 169.0, (qC) |
| 11-OAc | | | | 23.5 ($CH_3$) | | 23.4 ($CH_3$) | |
| | | | | 168.8 (qC) | | 168.0 (qC) | |
| 12-OAc | 2.07, ($CH_3$) | 20.7, ($CH_3$) | 20.6 ($CH_3$) | | | | |
| | 170.2, (qC) | 170.0, (qC) | 170.0 (qC) | | | | |
| 13-OAc | 21.4, ($CH_3$) | 21.4, ($CH_3$) | 21.1 ($CH_3$) | | | | |
| | 170.2, (qC) | 170.4, (qC) | 170.1 (qC) | | | | |

[a]Spectra recorded at 125 MHz in $CDCl_3$ at 25° C.
[b]Spectra recorded at 75 MHz in $CDCl_3$ at 25° C.
[c]Spectra recorded at 100 MHz in $CDCl_3$ at 25° C.
[d]Multiplicities deduced by DEPT.

TABLE 6

| <sup></sup>$^1$H NMR Data for compounds represented by formulae 5-9. | | | | | |
|---|---|---|---|---|---|
| position | 5[a] | 6[a] | 7[a] | 8[a] | 9[b] |
| 1 | 2.15, dd (11.6, 7.2)[c] | 2.16, dd (11.6, 6.8) | 2.18, (11.2, 6.8) | 2.55, dd (11.6, 7.6) | 2.55, dd (11.5, 7.5) |
| 2 | 3.54, s | 3.55, s | 3.57, s | 3.59, s | 3.60, s |
| 4 | 2.63, m | 2.64, m | 2.66, m | 2.25, m | 2.26, m |
| | 1.98, m | 2.00, m | 2.00, m | 1.71, m | 1.88, m |
| 5 | 1.46, m | 1.46, m | 1.49, m | α 2.12, m | α 2.15, m |
| | | | | β 1.70, m | β 1.52, m |
| 6 | 5.58 br s | 5.58, br s | 5.59, br s | 4.33, dd (10.4, 4.8) | 4.66, dd (11.5, 3.5) |
| 8α | 1.87, m | 1.89, m | 1.91, m | 2.44, d (14.0) | 2.51, d (14.5) |
| 8β | 1.96, m | 1.96, m | 1.98, m | 2.86, dd (14.0, 4.0) | 2.85, dd (14.0, 4.5) |
| 9 | 4.08, ddd (11.7, 8.0, 4.0) | 4.09, m | 4.11, m | 4.30, td (10.8, 4.0) | 4.29, td (11.0, 4.5) |
| 10 | 3.13, br t (7.2) | 3.14, br t (6.8) | 3.16, br t (6.8) | 2.66, dd (10.8, 7.6) | 2.66, dd (11.0, 7.5) |
| 12 | β: 2.21, m | β: 2.18, m | β: 2.21, m | 5.04, d (9.6) | 5.04, d (9.5) |
| | α: 1.38, m | α: 1.39, m | α: 1.42, m | | |
| 13 | 1.39, m | 1.41, m | 1.44, m | 5.49, dd (10.4, 10.4) | 5.49, dd (11.0, 10.0) |
| 14 | 1.16, m | 1.17, m | 1.20, m | 1.75, t (11.6) | 1.76, t (11.5) |
| 15 | 1.36, s | 1.37, s | 1.40, s | 1.61, s | 1.60, s |
| 16 | 1.16, s | 1.18, s | 1.22, s | 5.46, s; 5.12, s | 5.44, s; 5.22, s |
| 17 | 1.48, s | 1.49, s | 1.52, s | 1.17, s | 1.18, s |
| 18 | 1.73, m | 1.72, m | 1.73, m | 1.97, m | 1.96, m |
| 19 | 0.94, d (7.2) | 0.95, d (6.8) | 0.99, d (6.8) | 0.99, d (7.2) | 1.00, d (7.5) |
| 20 | 0.80, d (7.2) | 0.81, d (6.8) | 0.85, d (6.8) | 0.92, d (7.2) | 0.92, d (7.5) |
| 3-n-butyrate | 0.99, t (7.2) | 1.00, t (7.2) | 1.03, t (7.6) | 0.97, t (7.5) | 0.97, t (7.5) |
| | 1.67, m | 1.68, m | 1.71, m | 1.66, m | 1.67, m |
| | 2.38, m | 2.35, m | 2.36, m | 2.32, m | 2.31, m |
| 3' | 1.61, m | 1.63, m | 1.65, m | | |
| 2' | 2.31, m | 2.32, m | 2.32, m | | |
| 3" | 1.26, br s | 1.25, br s | 1.26, br s | | |
| 2" | 1.26, br s | 1.25, br s | 1.26, br s | | |
| 1" | 0.87, t (7.2) | 0.88, t (6.4) | 0.92, t (7.2) | | |
| 11-OAc | 1.98, s | 1.99, s | 2.02, s | | |
| 12-n-butyrate | | | | 0.91, t (7.2) | 0.91, t (7.0) |
| | | | | 1.58, m | 1.60, m |
| | | | | 2.13, m | 2.13, m |
| 13-OAc | | | | 2.00, s | 2.00, s |

[a]Spectra recorded at 400 MHz in $CDCl_3$ at 25° C.
[b]Spectra recorded at 500 MHz in $CDCl_3$ at 25° C.
[c]J values in Hz in parentheses.

TABLE 7

| $^1$H NMR Data for compounds represented by formulae 10-14. | | | | | |
|---|---|---|---|---|---|
| position | 10[a] | 11[b] | 12[a] | 13[c] | 14[a] |
| 1 | 2.55, dd (11.5, 7.5)[d] | 2.41, m | 2.47 m | 2.38 m | 2.82 m |
| 2 | 3.59, s | 3.55, s | 3.73 s | 5.17 d (6.4) | 5.29 d (9.0) |
| 4 | 2.24, m | 2.66, m | 2.44 m | 2.34 m | 2.10 m |
| | 1.71, m | 1.98, m | 2.19 m | 1.95 m | 1.83 m |
| 5 | α 2.12, m | α 1.57, m | 2.50 m | β 2.19 m | 2.25 m |
| | β 1.70, m | β 1.47, m | | α 1.40 m | 2.03 m |
| 6 | 4.33, dd (11.0, 4.0) | 5.61, d (5.4) | 9.70 br s | 3.28 dd (11.2, 4.0) | 5.24 dd (11.0, 4.5) |
| 8α | 2.44, d (14.5) | 1.81, m | 2.73 m | 1.99 m | 2.19 m |
| 8β | 2.86, dd (14.0, 5.0) | 1.93, m | | 1.03 m | 1.85 m |
| 9 | 4.28, dd (11.5, 3.5) | 4.29, td (10.8, 3.4) | 4.46 br t (8.5) | 1.33 m | 1.57 m |
| | | | | | 1.29 m |
| 10 | 2.67, dd (7.0, 11.0) | 2.63, br t (8.4) | 2.48 m | 2.96 m | 1.94 m |
| 12 | 5.01, d (10.0) | 5.02, d (9.6) | 5.04 d (9.5) | 1.90 m | 1.48 m |
| | | | | 1.56 m | |
| 13 | 5.49, dd (11.0, 10.0) | 5.48, dd (10.9, 9.9) | 5.45 t (11.0, 10.0) | 1.37 m | 1.53 m |
| | | | | | 1.42 m |
| 14 | 1.73, m | 1.74, m | 1.83 t (11.0) | 1.09 m | 0.94 m |
| 15 | 1.60, s | 1.39, s | 1.42 s | 1.70 s | 1.72 s |
| 16 | 5.46, s; 5.12, s | 1.19, s | 2.23 s | 1.17 s | 1.53 s |
| 17 | 1.18, s | 1.12, s | 1.14 s | 1.44 s | 1.25 s |
| 18 | 1.98, m | 1.72, m | 1.73 m | 1.92 m | 1.88 m |
| 19 | 0.99, d (7.5) | 1.01, d (7.0) | 1.01 d (7.5) | 0.92 d (6.8) | 0.98 d (7.0) |
| 20 | 0.92, d (7.5) | 0.96, d (7.0) | 0.88 d (7.5) | 0.69 d (6.8) | 0.77 d (7.0) |
| 3-n-butyrate | 0.93, t (7.0) | 0.99, t (7.1) | 0.99 t (7.5) | | |
| | 1.63, m | 1.69, m | 1.63 m | | |
| | 2.12, m | 2.37, m; 2.28, m | 2.26 m | | |

TABLE 7-continued

| $^1$H NMR Data for compounds represented by formulae 10-14. | | | | | |
|---|---|---|---|---|---|
| position | 10[a] | 11[b] | 12[a] | 13[c] | 14[a] |
| 6-OAc | | 2.09, s | | | |
| 11-OAc | | | | 2.01 s | |
| 12-OAc | 2.10, s | 2.08, s | 2.09 s | | |
| 13-OAc | 2.01, s | 1.99, s | 2.01 s | | |

[a]Spectra recorded at 500 MHz in $CDCl_3$ at 25° C.
[b]Spectra recorded at 300 MHz in $CDCl_3$ at 25° C.
[c]Spectra recorded at 400 MHz in $CDCl_3$ at 25° C.
[d]J values in Hz in parentheses.

TABLE 8

| $^1$H NMR Data for compounds represented by formulae 15-16. | | |
|---|---|---|
| position | 15[a] | 16[a] |
| 1 | 2.56, dd (12.0, 4.4)[b] | 2.34, dd (12.8, 6.4) |
| 2 | 3.90, s | 2.22, d (13.2) |
| 4 | 2.98, m<br>1.41, m | 2.15, m |
| 5 | 1.70, m | α 1.86, m<br>β 1.51, m |
| 6 | 3.85, dd (11.2, 6.0) | 4.35, dd (12.0, 5.2) |
| 8 | α 2.02, d (12.0)<br>β 2.79, d (12.0) | α 2.30, m<br>β 1.42, m |
| 9 | | 5.31, m |
| 10 | 4.06, d (4.4) | 1.94, d (5.6) |
| 12 | 2.26, dd (9.6, 3.6) | 1.59, m<br>1.54, m |
| 13 | 1.65, m<br>1.23, m | 1.57, m<br>1.37, m |
| 14 | 1.98, m | 1.15, m |
| 15 | 1.55, s | 4.84, s<br>4.66, s |
| 16 | 1.16, s | 0.86, s |
| 17 | 1.49, s | 1.32, s |
| 18 | 1.92, m | 1.80, m |
| 19 | 1.01, d (6.8) | 0.90, d (6.8) |
| 20 | 0.76, d (6.8) | 0.87, d (6.8) |
| 3-n-butyrate | 1.05, t (7.2)<br>1.75, m<br>2.45, m | |
| 4-n-butyrate | | |
| 9-OAc | | 2.08, s |
| 11-OAc | 2.02, s | |
| 12-OAc | | |
| 13-n-butyrate | | |
| 7-OH | 4.88, s | |

[a]Spectra recorded at 500 MHz in $CDCl_3$ at 25° C.
[d]J values in Hz in parentheses.

Anti-Inflammation Assay In Vitro

A mouse macrophage cell line, RAW 264.7, purchased from the American Type Culture Collection (ATCC, No TIB-71) was chosen in the in vitro model. The cells were cultured in DMEM (Dulcbecco/s Modified Eagle medium) containing 10% fetal bovine serum (FBS) and penicillin G (100 U/ml) and streptomycin (100 μg/ml) at 37° C. and 5% $CO_2$. When reaching 80% confluence, the cells were subcultured with trypsin. The cells were subjected to an anti-inflammation assay after subcultured for 36 hours. $3\times10^6$ RAW264.7 cells were cultured in a 10-cm culture dish and administered with lipopolysaccharide (LPS, 0.01 μg/ml; Sigma L2654). After 16 hours, the cells were collected. In an experiment group, the compound represented by formula 3 was added into the culture dish and followed by LPS before 10 minutes.

Assay for Protein Expression of Inducible Nitric Oxide Synthase and/or Cyclooxygenase-2

The collected RAW264.7 cells were dissolved with 200 μL of 4° C. lysis buffer (50 mM Tris [pH 7.5], 150 mM NaCl, 1% TritonX-100, 0.1 mM EDTA, 0.1 mM EGTA, 10 μg PMSF, 1 aprotinin, 20 mM NaF, and 0.2 mM $Na_3VO_4$). The samples were centrifuged at 25,000 g for 30 minutes at 4° C. for removing the pellet. The supernatant was assayed with Bio-Rad DC protein assay kit (Bio-Rad Laboratories, Hercules, Calif., USA) and the absorbance was read with an ELISA reader (Thermo Electron Corporation, USA) for estimating the protein contents. The calibrated samples with equal volumes were added with a sample buffer (2% SDS, 10% glycerol, 0.1% bromophenol blue, 10% 2-mercaptoethanol, and 50mM Tris) of the same volume. Proteins were separated with 10% SDS-PAGE and transferred to a PVDF membrane (0.45 mm, Immobilon-P, Millipore, Bedford, Mass., USA) (1.5 A, 4° C., 2.5 hours). The transferred PVDF membranes were blocked with TTBS (Tris-HCl 20 mM, NaCl 137 mM, pH 7.4 and 0.1% Tween 20) containing 5% skim milk at room temperature for 1 hour and reacted with polyclonal anti-inducible nitric oxide synthase antibody (Transduction Laboratories, Lexington, Ky., USA) or polyclonal anti-cyclooxygenase-2 antibody (Cayman, Ann Arbor, Mich., USA) at room temperature for 3 hours. After washed with TTBS three times, the samples were reacted with HRP-conjugated anti-rabbit IgG antibody (1:2000) at room temperature for 1 hour. After washed with TTBS for three times, an enhanced chemiluminescence detection kit was used for reating with the PVDF membrane and exposed with an X-ray film (Kodak X-OMAT LS, Kodak, Rochester, N.Y., USA) for detecting the protein expression. The relative amount was calculated with Image-Pro plus 4.5 software (Media Cybernetics, Silver Spring, USA). The group added with only LPS was taken as 100%. β-actin (monoclonal antibody, Sigma, St Louis, Mo., USA) was taken as an internal control.

Cytotoxicity Testing.

Cell lines were purchased from the American Type Culture Collection (ATCC). Cytotoxicity assays were performed using the MTT [3-(4,5-dimethylthiazol-2-yl)-2,5-diphenyltetrazolium bromide] colorimetric method.

The anti-inflammatory activity of the compounds represented by formulae 2-4 against the accumulation of pro-inflammatory iNOS and COX-2 proteins in RAW264.7 macrophage cells stimulated with LPS was evaluated using immunoblot analysis. At a concentration of 10 mM (FIG. 1), compounds represented by formulae 2-4 were found to significantly reduce the levels of iNOS protein to 8.8±1.0%, 17.8±4.7%, and 11.3±1.5%, respectively, relative to control cells stimulated with LPS only. At the same concentration, compounds represented by formula 4 also significantly reduced COX-2 expression (7.2±2.5%) by LPS treatment.

Cytotoxicity of compounds represented by formulae 5-16 toward a limited panel of cancer cell lines was evaluated. The results showed that compound represented by formula 13 exhibited weak cytotoxicity toward Hep G2 and Hep 3B (human hepatocellular carcinoma), MDA-MB-231 and MCF-7 (human breast carcinoma), A549 (human lung carcinoma), and Ca9-22 (human gingival carcinoma) cell lines with $IC_{50}$'s of 18.5, 12.2, 15.3, 12.7, 14.1, and 14.1 μg/mL, respectively. Also, compound represented by formula 16 showed weak cytotoxicity ($IC_{50}$'s 12.5, 9.6, 16.0, 9.9, 15.3 and 13.6 μg/mL) against the growth of Hep G2, Hep 3B, MDA-MB-231, MCF-7, A549, and Ca9-22 cells, respectively. Other compounds were found to be inactive against the growth of the above six cancer cells.

Figure 2:
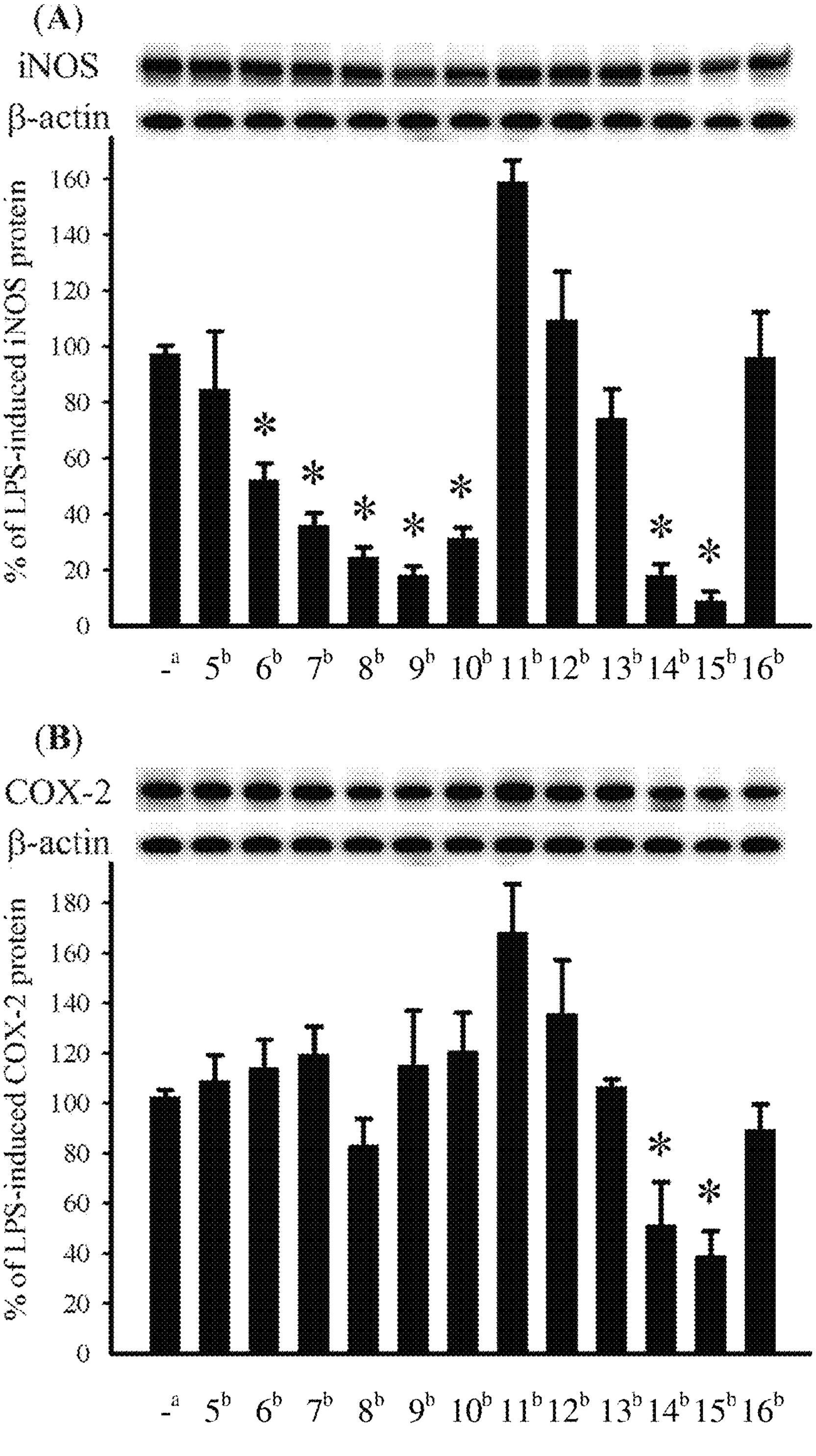
FIG. 2 shows the effect of the compounds represented by formulae 5-16 on iNOS and COX-2 protein expression of RAW264.7 macrophage cells by immunoblot analysis. (A) Immunoblots of iNOS and β-actin; (B) Immunoblots of COX-2 and β-actin. The values are mean±SEM. (n=6). Relative intensity of the LPS alone stimulated group was taken as 100%. Under the same experimental condition CAPE (caffeic acid phenylethyl ester, 10 μM) reduced the levels of the iNOS and COX-2 to 2.5±3.7% and 67.2±13.4%, respectively. *Significantly different from LPS alone stimulated group (*P<0.05). [a]stimulated with LPS, stimulated with LPS in the presence of 1-12 (10 μM).

The in vitro anti-inflammatory effects of compounds represented by formulae 5-16 were also tested. In this assay, the inhibition of LPS-induced up-regulation of pro-inflammatory proteins, iNOS and COX-2 in RAW264.7 macrophage cells was measured by immunoblot analysis. At a concentration of 10 μM, compounds represented by formulae 5-16, in particular 6-10, 14, and 15 were found to significantly reduce the expression of iNOS protein, relative to the control cells stimulated with LPS only. Furthermore, at the same concentration, compounds represented by formulae 14-15 also could effectively reduce COX-2 expression in the same macrophage cells with LPS treatment. On the other hand, compound represented by formula 11 could enhance the expression of both iNOS and COX-2 which might be arisen from the presence of acetoxy and hydroxy groups at C-6 and C-7, respectively (FIG. 2).

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for preparing a purified compound represented by the following formula, formula 1

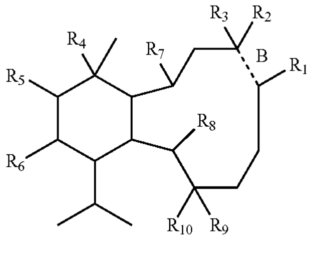

$R_1$ is selected from the group consisting of —H, —OH, —OC(═O)$R_{11}$, —OOH, and OAc;

$R_2$ is selected from the group consisting of —S(C═O)$CH_3$ and —OH;

$R_3$ is selected from the group consisting of —$CH_3$ and —OH; $R_4$ is selected from the group consisting of —OH and —OAc;

$R_5$ is selected from the group consisting of —H, —OAc, and —OC(═O)CH2CH2$CH_3$;

$R_6$ is selected from the group consisting of —H, —OC(—O)$CH_2CH_2CH_3$, OC(═O)$CH_2CH_2$S(═O)CH3, and —OAc;

$R_7$ is selected from the group consisting of —H, —OAc, and ═O;

$R_8$ is —H;

$R_9$ is —OC(═O)$CH_2CH_2CH_3$;

$R_{10}$ is —$CH_3$;

$R_{11}$ is an alkyl group; and

B is a single bond; or $R_1$ and $R_1$ together form the group consisting of —O— and a double bond; or $R_2$ and $R_3$ together form ═$CH_2$, $R_4$ is OH and $R_6$ is OAc; or $R_7$ and $R_8$ together form —O—; or $R_8$ and $R_9$ together form a double bond; or $R_1$ and $R_8$ together form —O—; or $R_9$ and $R_{10}$ together form ═$CH_2$; or $R_2$ and $R_8$ together form a single bond; or $R_2$ and B together form ═O and $R_1$ and B together form ═O;

wherein the compound is not the compound represented by the following formula 17 or 18;

formula 17

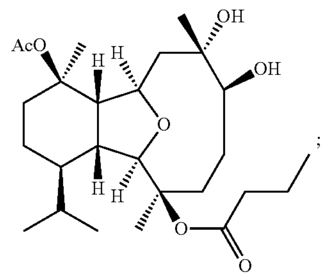

;

formula 18

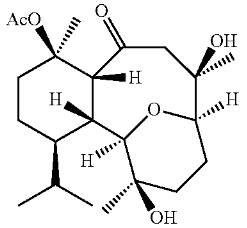

comprising obtaining the compound from an extract of cultured *Klyxum simplex*.

2. The method according to claim 1, wherein the organic solvent is selected from the group consisting of an alcohol, an ester, a ketone, an ether, chloroform, dichloromethane, and benzene.

3. The method according to claim 1, wherein cultured *Klyxum simplex* is freeze-dried before step (a).

4. A method for treating inflammation, atherosclerosis, neuropathic pain, inflammatory neointimal proliferation, arthritis, multiple sclerosis, inflammatory pain, and/or spinal cord injury comprising administering a subject with a purified compound represented by the following formula, formula 1

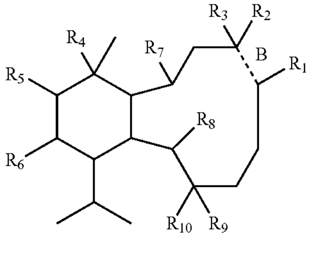

$R_1$ is selected from the group consisting of —H, —OH, —OC(═O)$R_{11}$, —OOH, and OAc;

$R_2$ is selected from the group consisting of —S(C═O)$CH_3$ and —OH;

$R_3$ is selected from the group consisting of —$CH_3$ and —OH; $R_4$ is selected from the group consisting of —OH and —OAc;

$R_5$ is selected from the group consisting of —H, —OAc, and —OC(═O)CH2CH2$CH_3$;

$R_6$ is selected from the group consisting of —H, —OC(—O)$CH_2CH_2CH_3$, OC(═O)$CH_2CH_2$S(═O)CH3, and —OAc;

$R_7$ is selected from the group consisting of —H, —OAc, and ═O;

$R_8$ is —H;

$R_9$ is —OC(═O)$CH_2CH_2CH_3$;

$R_{10}$ is —$CH_3$;

$R_{11}$ is an alkyl group; and

B is a single bond; or $R_1$ and $R_1$ together form the group consisting of —O— and a double bond; or $R_2$ and $R_3$ together form ═$CH_2$, $R_4$ is OH and $R_6$ is OAc; or $R_7$ and $R_8$ together form —O—; or $R_8$ and $R_9$ together form a double bond; or $R_1$ and $R_8$ together form —O—; or $R_9$ and $R_{10}$ together form ═$CH_2$; or $R_2$ and $R_8$ together form a single bond; or $R_2$ and B together form ═O and $R_1$ and B together form ═O;

wherein the compound is not the compound represented by the following formula 17 or 18;

formula 17

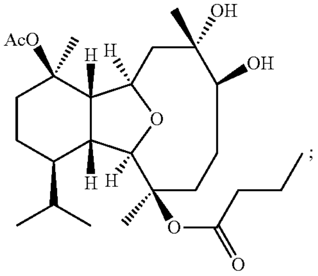

formula 18

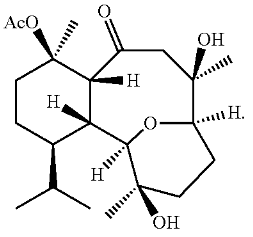

5. The method according to claim 4, wherein the purified compound is administered by injection.

6. A method for treating inflammation, atherosclerosis, neuropathic pain, inflammatory neointimal proliferation, arthritis, multiple sclerosis, inflammatory pain, and/or spinal cord injury comprising administering a subject with An extract of cultured *Klyxum simplex* comprising the purified compound represented by the following formula, formula 1

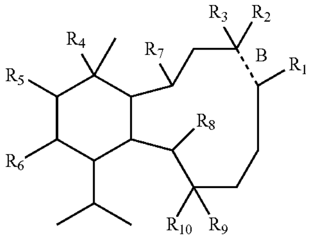

$R_1$ is selected from the group consisting of —H, —OH, —OC(═O)$R_{11}$, —OOH, and OAc;

$R_2$ is selected from the group consisting of —S(C═O)$CH_3$ and —OH;

$R_3$ is selected from the group consisting of —$CH_3$ and —OH; $R_4$ is selected from the group consisting of —OH and —OAc;

$R_5$ is selected from the group consisting of —H, —OAc, and —OC(═O)CH2CH2$CH_3$;

$R_6$ is selected from the group consisting of —H, —OC(—O)$CH_2CH_2CH_3$, OC(═O)$CH_2CH_2$S(═O)CH3, and —OAc;

$R_7$ is selected from the group consisting of —H, —OAc, and ═O;

$R_8$ is —H;

$R_9$ is —OC(═O)$CH_2CH_2CH_3$;

$R_{10}$ is —$CH_3$;

$R_{11}$ is an alkyl group; and

B is a single bond; or $R_1$ and $R_1$ together form the group consisting of —O— and a double bond; or $R_2$ and $R_3$ together form ═$CH_2$, $R_4$ is OH and $R_6$ is OAc; or $R_7$ and $R_8$ together form —O—; or $R_8$ and $R_9$ together form a double bond; or $R_1$ and $R_8$ together form —O—; or $R_9$ and $R_{10}$ together form ═$CH_2$; or $R_2$ and $R_8$ together form a single bond; or $R_2$ and B together form ═O and $R_1$ and B together form ═O;

wherein the compound is not the compound represented by the following formula 17 or 18;

formula 17

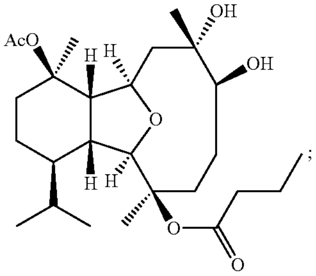

-continued
formula 18
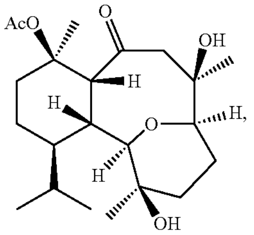
wherein the disease associated with inducible nitric oxide synthase and/or spinal cord injury.
7. The method according to claim 6, wherein the extract is administered by injection.
* * * * *